(12) United States Patent
Sengun

(10) Patent No.: US 9,451,953 B2
(45) Date of Patent: Sep. 27, 2016

(54) KNOTLESS COLLAPSIBLE SUTURES AND METHODS FOR SUTURING

(71) Applicant: DePuy Mitek, LLC, Raynham, MA (US)

(72) Inventor: Mehmet Z. Sengun, Canton, MA (US)

(73) Assignee: DePuy Mitek, LLC, Raynham, MA (US)

( * ) Notice: Subject to any disclaimer, the term of this patent is extended or adjusted under 35 U.S.C. 154(b) by 117 days.

(21) Appl. No.: 14/102,915

(22) Filed: Dec. 11, 2013

(65) Prior Publication Data

US 2015/0157308 A1    Jun. 11, 2015

(51) Int. Cl.
 *A61B 17/04* (2006.01)
 *A61L 17/00* (2006.01)
 *A61B 17/06* (2006.01)

(52) U.S. Cl.
 CPC ...... *A61B 17/06166* (2013.01); *A61B 17/0485* (2013.01); *A61B 2017/06176* (2013.01); *A61B 2017/06185* (2013.01)

(58) Field of Classification Search
 CPC .............. A61B 17/04; A61B 17/0469; A61B 17/0482; A61B 17/0485; A61B 17/06166; A61B 2017/06176; A61B 2016/06185
 See application file for complete search history.

(56) References Cited

U.S. PATENT DOCUMENTS

| 3,072,986 | A | 1/1963 | Lefnaer |
| 3,224,054 | A | 12/1965 | Lige |
| 5,053,047 | A | 10/1991 | Yoon |
| 5,123,913 | A | 6/1992 | Wilk et al. |
| 5,683,417 | A | 11/1997 | Cooper |
| 6,296,659 | B1 * | 10/2001 | Foerster .................. 606/224 |
| 7,967,841 | B2 | 6/2011 | Yuan et al. |
| 8,267,961 | B2 | 9/2012 | Popadiuk et al. |
| 2007/0005110 | A1 | 1/2007 | Collier et al. |
| 2008/0132943 | A1 | 6/2008 | Maiorino et al. |
| 2009/0099597 | A1 | 4/2009 | Isse |
| 2009/0299407 | A1 | 12/2009 | Yuan et al. |
| 2009/0306710 | A1 | 12/2009 | Lindh, Sr. et al. |

(Continued)

FOREIGN PATENT DOCUMENTS

| EP | 2 404 557 A1 | 1/2012 |
| EP | 2 662 032 A1 | 11/2013 |
| WO | 0152751 A1 | 7/2001 |

OTHER PUBLICATIONS

STRATAFIX Product Catalog, SFX-396-12, Ethicon Inc, 2012 (2 pages).

(Continued)

*Primary Examiner* — Melanie Tyson

(57) ABSTRACT

Various exemplary methods and devices are provided for improved surgical sutures, suture systems, and methods for suturing. In general, the sutures, suture systems, and methods can allow a suture to form a secure, closed loop without tying a knot. The suture can include a barbed portion configured to be threaded through a hollow portion. The barbed portion can have a plurality of barbs thereon, which can grasp onto an inner wall of the hollow portion when disposed therein to help secure the loop at a desired size. The barbs can all be oriented in one direction that corresponds to a direction of movement of the suture when the loop is being tightened. Thus, the barbs can be configured to allow for a size of the loop to be easily reduced to any desired size to approximate tissue, but can be configured to resist subsequent expansion of the loop to ensure that the tissue remains in place.

19 Claims, 3 Drawing Sheets

(56) References Cited

U.S. PATENT DOCUMENTS

| | | |
|---|---|---|
| 2009/0312791 A1 | 12/2009 | Lindh, Sr. et al. |
| 2010/0298871 A1 | 11/2010 | Ruff et al. |
| 2011/0048216 A1 | 3/2011 | Lindh, Sr. et al. |
| 2011/0270278 A1 | 11/2011 | Overes et al. |
| 2011/0282384 A1* | 11/2011 | Odermatt et al. ............ 606/222 |
| 2012/0277770 A1 | 11/2012 | Fenton et al. |
| 2014/0257379 A1 | 9/2014 | McClellan et al. |

OTHER PUBLICATIONS

The STRATAFIX Knotless Tissue Control Device platform offers a wide range of products appropriate for multiple surgical applications, SFK-019-13, Ethicon, Inc, 2013 (2 pages).

STRATAFIX Knotless Tissue Control Devices—a portfolio of products appropriate for a broad range of surgical applications, SFX-376-12, Ethicon, Inc, 2012 (2 pages).

STRATAFIX Knotless Tissue Control Devices—a portfolio of products appropriate for a broad range of surgical applications including total hip replacement and total knee replacement, SFX-365-12, Ethicon, Inc, 2012 (2 pages).

ETHIBOND EXCEL Polyester Suture—Description & Specs, Ethicon, Inc (Retrieved from http://www.ethicon.com/healthcare-professionals/products/wound-closure/non-absorbable-sutures/ethibond-excel-polyester#!description-and-specs on Oct. 21, 2013) (2 pages).

Ethibond Excel Polyester Suture—About, Ethicon, Inc (Retrieved from http://www.ethicon.com/healthcare-professionals/products/wound-closure/non-absorbable-sutures/ethibond-excel-polyester#!overview on Oct. 21, 2013 ) (1 page).

Extended European Search Report for Application No. 14197235.6, issued Apr. 22, 2015 (10 pages).

* cited by examiner

KNOTLESS COLLAPSIBLE SUTURES AND METHODS FOR SUTURING

FIELD

The present disclosure relates generally to surgical sutures, suture systems, and methods for suturing.

BACKGROUND

The rotator cuff, a group of four muscles that wrap around the shoulder joint to attach the upper arm to the shoulder blade, in part allows the shoulder to move and turn through a wider range than any other joint in the body. Unfortunately, tears of the rotator cuff are common, making many routine activities difficult and painful.

Rotator cuff tears are treated through physical rehabilitation with limited success, and as such, surgery is often necessary to correct the function of the muscle group. Rotator cuff repair surgery can be done either through a traditional large incision, or arthroscopically using three to four small incisions and a keyhole camera. Large surgical incisions can cause significant pain and require lengthy recovery times, and thus arthroscopic procedures are generally preferred.

Although the goal to re-attach the torn rotator cuff muscle is the same using all methods, decreasing the size of the incision used increases the level of surgical skill required. It can be difficult to manipulate sutures and properly adjust the tension of suture knots within the surgical site using arthroscopic techniques. Further, knots and other bulky attachment means can irritate tissue over time. Sutures can be similarly difficult to secure and/or similarly irritating to tissue in other surgical applications, such as in anterior cruciate ligament (ACL) repair.

Accordingly, there is a need for improved surgical sutures, suture systems, and methods for suturing.

SUMMARY

Sutures, suture systems, and methods are generally provided for securing tissue to adjacent tissue and/or to bone. In one embodiment, a suturing system is provided that includes a flexible suture having leading and trailing ends. The suture can have a first partial longitudinal length with a plurality of unidirectional barbs, and a second partial longitudinal length having a hollow portion. The hollow portion can be located between the trailing end of the suture and the plurality of unidirectional barbs, and the leading end of the suture can be configured to pass through the hollow portion so as to move at least one of the barbs into the hollow portion such that the at least one of the barbs grasps onto the suture within the hollow portion thereof. In some embodiments, the suture can be a single strand including the barbs and the hollow portion.

The suturing system can have various configurations. In some embodiments, the barbs can be configured to grasp soft tissue so as to prevent movement of the suture relative to the soft tissue in a direction opposite to the unidirection of the barbs. In some embodiments, when the at least one of the barbs are positioned within the hollow portion, the first partial longitudinal length can be coaxial with the hollow portion of the second partial longitudinal length. In some embodiments, the first partial longitudinal length of the suture can be longer than the hollow portion of the second partial longitudinal length of the suture. The suture can include a third partial longitudinal length that extends between the barbs and the leading end. The respective lengths can vary, and in one embodiment the third partial longitudinal length can be longer than each of the first and second partial longitudinal lengths of the suture.

The system can include a threader positioned within the hollow portion of the suture. The leading end of the suture can be configured to mate to the threader, which can be configured to be pulled through the hollow portion of the suture with the leading end mated therewith so as to pass the leading end of the suture into the hollow portion and move the leading end therethrough such that at least one of the barbs is moved into the hollow portion.

The system can include a cannula. The suture can be configured to pass through the cannula, into a soft tissue, and back through the cannula so as to position a free end of the suture outside the cannula and to position the barbs outside the soft tissue. The free end of the suture that is positioned outside the cannula can be configured to be moved relative to the cannula so as to move the barbs into the soft tissue and into the hollow portion of the suture.

In another embodiment, a suturing system is provided that includes a flexible suture having a free end configured to enter into a hollow portion of the suture and pass through the hollow portion in a first direction so as to move a plurality of unidirectional barbs extending outward from the suture along a length of the suture into the hollow portion. The barbs can be configured to grasp onto the suture within the hollow portion so as to prevent the length of the suture from moving within the hollow portion in a second direction that is opposite to the first direction.

The system can vary in a number of ways. In some embodiments, the barbs can extend along a length of the suture that is greater than a length of the hollow portion such that all of the barbs cannot be simultaneously positioned within the hollow portion. In some embodiments, the barbs positioned within the hollow portion that grasp onto the suture within the hollow portion can be configured to lock the length of the suture in a fixed position relative to the hollow portion of the suture. In some embodiments, a length of the suture can be positioned within the hollow portion, and the length of the suture can be coaxial with the hollow portion of the suture. In some embodiments, the barbs can be configured to grasp soft tissue so as to prevent movement of the suture relative to the soft tissue in a direction opposite to the unidirection of the barbs.

The system can include a threader that can be positioned within the hollow portion of the suture. The free end of the suture can be configured to mate to the threader, which can be configured to be pulled through the hollow portion with the free end mated therewith so as to pass the free end of the suture into the hollow portion and position one or more of the barbs within the hollow portion.

The system can include a cannula. The suture can be configured to pass through the cannula, into a soft tissue, and pass back through the cannula so as to position a free end of the suture outside the cannula and to position the barbs outside the soft tissue. The free end that is positioned outside the cannula can be configured to be moved relative to the cannula so as to move the barbs into the soft tissue and into the hollow portion of the suture.

In another aspect, surgical methods are provided that in one embodiment includes advancing a leading end of a suture into a first tissue, advancing the leading end of the suture into a second tissue, and advancing the leading end of the suture into a hollow portion of the suture so as to form a loop. The method can also include pulling the leading end of the suture relative to the hollow portion, the first tissue, and the second tissue so as to advance a plurality of unidirectional barbs formed on the suture through the first tissue, through the second tissue, and into the hollow portion. The plurality of unidirectional barbs can grasp the second tissue and can grasp the suture within the hollow portion so as to lock the suture in position relative to the first and second tissues.

The method can have any number of variations. In some embodiments, a length of the suture extending through the hollow portion can be coaxial with the hollow portion. In some embodiments, the leading end of the suture can be advanced into the hollow portion of the suture after the leading end of the suture has been advanced into the first tissue and advanced into the second tissue. In some embodiments, the method can also include advancing the leading end of the suture through a cannula prior to advancing the leading end into the first tissue, and advancing the leading end of the suture back into the cannula after advancing the leading end into the second tissue. In some embodiments, pulling the leading end of the suture can cause the first and second tissues to be drawn together.

BRIEF DESCRIPTION OF DRAWINGS

This invention will be more fully understood from the following detailed description taken in conjunction with the accompanying drawings, in which.

DETAILED DESCRIPTION

Figure 1:
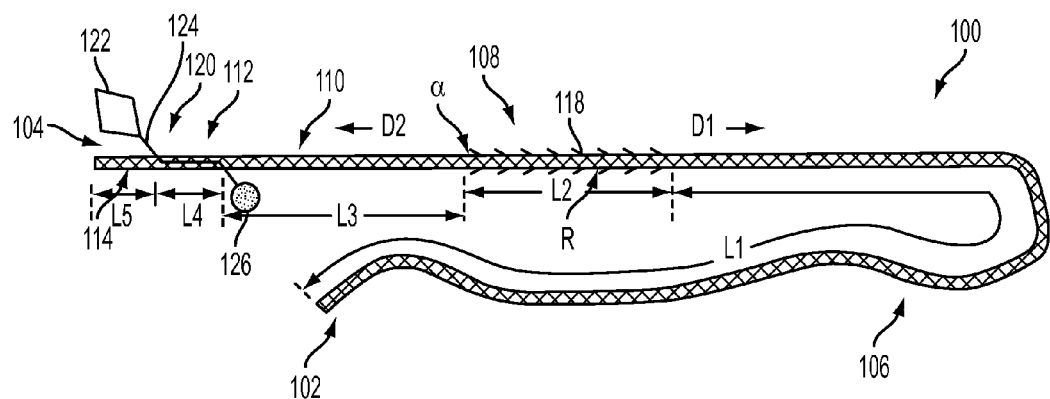
FIG. 1 is a side schematic view of one embodiment of a suture, the suture having a threader mated thereto.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

To the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary methods and devices are provided for improved surgical sutures, suture systems, and methods for suturing. In general, the sutures, suture systems, and methods can allow a suture to form a secure, closed loop without tying a knot. The suture can include a barbed portion that is configured to be threaded through a hollow portion of the suture to form a closed loop. The barbed portion can have a plurality of barbs thereon, which can be configured to grasp onto an inner wall of the hollow portion when disposed therein to help secure the loop at a desired size. Multiple barbs can be disposed within the hollow portion when the loop is at the desired size, thus creating multiple points of contact between the barbed and hollow portions. This can increase a load-bearing capacity of the loop and/or can reduce a risk of the loop being loosened. To further help secure the loop of suture at the desired size, the barbs can all be oriented in one direction that corresponds to a direction of movement of the suture when the loop is being tightened. Thus, when the suture is moved and/or tensioned in the direction of the barbs, the barbs can be configured to allow for the barbed portion to pass easily through the hollow portion. When the suture is tensioned in a direction that is opposite to the direction of the barbs, the barbs can be configured resist movement of the barbed portion within the hollow portion. In this way, the barbs can be configured to allow for a size of the loop to be easily reduced to any desired size to approximate tissue, but can be configured to resist subsequent expansion of the loop to ensure that the tissue remains in place.

In an exemplary embodiment, shown in FIG. 1, a suture 100 can include a barbed portion 108 and a hollow portion 12 disposed between a leading end 102 and a trailing end 104 of the suture 100. Interspersed between the barbed and hollow portions 108, 112, there can be non-hollow portions of varying lengths. As in the illustrated embodiment, the suture 100 can include a non-hollow leading portion 106 adjacent to the leading end 102, a non-hollow intermediate portion 110 disposed between the barbed portion 108 and the hollow portion 112, and a non-hollow trailing portion 114 disposed between the hollow portion 112 and the trailing end 104. Both the leading and barbed portions 106, 108 can be configured to be threaded through the hollow portion 112 to form a closed loop. When barbs 118 of the barbed portion 108 are disposed within the hollow portion 112, they can grasp onto the hollow portion 112 to secure the loop at a desired size. In this way, the suture 100 can have a self-locking mechanism, in which one portion of the suture 100, e.g., the hollow portion 112, is configured to lock to another portion of the suture 100, e.g., the barbed portion 108, without the use of a knot and/or any other attachment mechanisms, e.g., adhesive, clips, etc.

The suture 100 can have a variety of shapes and sizes. In general, the suture 100 can be configured to pass through tissue. The suture 100 can have any length sufficient to allow for the suture 100 to be manipulated by a user and passed through tissue, as will be appreciated by a person skilled in the art. The suture 100 can have any width, either constant or varying, along the length of the suture 100. In one exemplary embodiment, a width of one or both of the barbed portion 108 and the leading portion 106 can be less than a width of the hollow portion 112, which can facilitate passage of the leading and barbed portions 106, 108 through the hollow portion 112. Although the suture 100 is a single strand in the illustrated embodiment, the suture 100 can include more than one suture strand. By way of non-limiting example, the leading portion 106 and/or the barbed portion 108 can include a second suture strand that is attached to a first suture strand that includes the hollow portion 112.

The suture 100 can be made from any one or more materials, as will be appreciated by a person skilled in the art. The material(s) can be flexible such that the suture 100 is sufficiently flexible to allow the barbed and leading portions 108, 106 to pass through the hollow portion 112 and to form a loop of a desired size.

The barbed portion 108 of the suture 100 can extend along any length of the suture 100. In the illustrated embodiment, the barbed portion 108 extends along a partial length L2 of the suture 100. The barbed portion's length L2 can be sized in accordance with a type of tissue that the suture 100 can be configured to approximate and/or can be sized sufficiently large to tolerate a range of tissue thicknesses. For example, the barbed portion's length L2 can be large so as to facilitate use of the suture 100 with very thick tissue and/or different types of tissue. The barbed portion's length L2 can be larger than a length L4 of the hollow portion 112, as in the illustrated embodiment, such that all of the barbs 118 disposed on the barbed portion 108 cannot be disposed within the hollow portion 112 at the same time. Because it can be difficult to predict a desired size of the loop prior to the loop being formed and tightened, a longer length L2 of the barbed portion 108 can help ensure that at least some of the barbs 118 are disposed within the hollow portion 112 when the loop is reduced to the desired size. In an exemplary embodiment, the relative lengths L2 and L4 of the barbed portion 108 and the hollow portion 112 can be sized to allow for the barbed portion 108 to extend coaxially all the way through the hollow portion 112 when the suture 100 is arranged in a loop of the desired size, thus maximizing the number of barbs 118 contained within the hollow portion 112 so as to help securely form the loop and prevent slippage thereof. Any barbs 118 that are not encompassed in the hollow portion 112 can dig into tissue through which the suture 100 passes, further helping to secure the loop of the suture 100 against movement relative to the tissue.

The leading, intermediate, and trailing portions 106, 110, 114 can each have any length. The leading portion 106 can have a length L1 that is greater than each of the lengths L2 and L4 of the barbed and hollow portions 108, 112, respectively. The larger the leading portion's length L1, the easier it can be for a user to manipulate the suture 100 to pass the suture 100 through tissue. Particularly during arthroscopic procedures, where the tissue to be approximated can be located far from a surgical opening, a large length L1 of the leading portion 106 can facilitate manipulation of the suture 100 through the tissue. By way of non-limiting example, where a cannula is used to access a surgical site, as discussed further below, the leading portion's length L1 can be large enough to allow for the suture 100 to pass down through the cannula, through the target tissue, and back up through the cannula with the barbs 118 and/or the leading end 102 positioned entirely outside the cannula. This can help to reduce a risk of incidental damage to the tissue by the barbs 118. The intermediate and trailing portions 110, 114 can have lengths L3 and L5, respectively, which can each be less than the length L1 of the leading portion 106.

In an exemplary embodiment, the length of the suture 100 can be in a range of about 100 to 1500 mm, the length L2 of the barbed portion 108 can be in a range of about 10 to 100 mm, the length L4 of the hollow portion 112 can be in a range of about 5 to 50 mm, e.g., in a range of about 5 to 10 mm, the length L1 of the leading portion 106 can be in a range of about 100 to 1500 mm, the length L3 of the intermediate portion 110 can be in a range of about 1 to 100 mm, and the length L5 of the trailing portion 114 can be in a range of about 5 to 25 mm.

Figure 2:
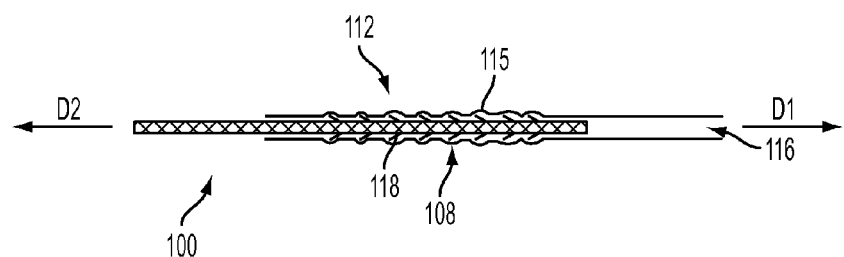
FIG. 2 is a side schematic view of a portion of the suture of FIG. 1 with end portions of the suture being locked together.

The hollow portion 112 can generally be configured to allow for passage of the length L1 of the leading portion 106 and a partial length of the barbed portion 108 therethrough and to allow for securing the barbed portion 108 therein. The barbed portion 108 can be configured to be positioned coaxially within the hollow portion 112, as shown in FIG. 2. As also shown in FIG. 2, the hollow portion 112 can have an inner passageway 116 that extends longitudinally therethrough. The passageway 116 can be wide enough and long enough to coaxially seat at least a portion of the barbed portion 108 therein. Similarly, an outer wall 115 of the hollow portion 112 can be configured to allow for passage of the barbed portion 108 therethrough. A weave of the wall 115 of the hollow portion 112 can be loose enough to allow for passage of the barbed portion 108 through the wall 115 of the hollow portion 112. In some embodiments, e.g., where the hollow portion 112 is a braided suture, a weave of the hollow portion 112, e.g., of the braid, can be loose enough to allow for the barbs 118 to stick out of hollow portion 112 and through the wall 115 when the barbed portion 108 is seated coaxially within the hollow portion 112, which can help to further secure the suture 100 to tissue by allowing the barbs 108 extending through the wall 115 to dig into the tissue. The hollow portion 112 can be made from one or more materials that can be different from one or more materials used to make the barbed portion 108 and/or the leading portion 106. In one embodiment, the hollow portion 112 can be made from one or more materials sufficiently flexible to allow for expansion and restriction of the passageway 116 and/or of spaces in the wall 115 as the barbed portion 108 passes therethrough. In an exemplary embodiment, the hollow portion 112 can be the Ethibond™ #5 coreless suture, available from Ethicon, Inc. of Somerville, N.J., with its core removed.

The barbed portion 108 can have a plurality of barbs 118 thereon. There can be any number of barbs 118, oriented in any pattern along the length L2 of the barbed portion 108. In the illustrated embodiment, there are eight pairs of barbs 118, each pair extending from the same longitudinal position on the suture 100 and from opposite sides of the suture 100. The barbs 118 can be long enough and wide enough to grasp onto the hollow portion 112 when the barbed portion 108 is disposed therein and/or to grasp onto tissue through which the barbed portion 108 passes. The barbs 118 can be small enough to allow for passage of the barbed portion 108 through the passageway 116 and the wall 115 of the hollow portion 112. In an exemplary embodiment, only the barbs 118 of the barbed portion 108 can extend through the wall 115 when the barbed portion 108 is positioned within the hollow portion 112, such that a core portion of the barbed portion 108 from which the barbs 118 extend can be contained within the hollow portion 112. The barbs 118 can be unidirectional, such as in the illustrated embodiment in which the barbs 118 all extend radially outward from the suture 100 in a first direction D1. The first direction D1 can correspond to a direction in which the suture 100 is moved to tighten a loop of the suture 100. The barbs 118 can extend at an angle α relative to the suture 100, which can be any angle, either the same or different from one another. In an exemplary embodiment, all of the barbs 118 can extend outwardly from the suture 100 at the same angle α. The angle α must be small enough to allow for passage of the barbs 118 through the wall 115 and the passageway 116 of the hollow portion 112 when the barbed portion 108 is moved through the hollow portion 112 in the first direction D1, but must be large enough to cause the barbs 118 to catch on the wall 115 and/or the passageway 116 when the barbed portion 108 stops being moved through the hollow portion 112 and if the suture 100 is pulled in a second direction D2 that is opposite to the first direction D1. Thus, the barbs 118 can allow for a size of the loop to be easily reduced to any desired size to approximate tissue but can resist subsequent expansion of the loop to ensure that the suture 100 remains in place relative to the tissue. The barbs 118 can be arranged in any pattern along the length of the suture 100, in any longitudinal position and at any angle α to achieve a desired amount of resistance to movement in the second direction D2.

FIG. 2 illustrates the barbed portion 108 passed coaxially through the hollow portion 112. As shown in FIG. 2, the barbs 118 can dig into the wall 115 along multiple points of contact to resist movement of the suture 100 in the second direction D2 so as to help prevent expansion of the size of the loop. The barbs 118 can also be configured to help secure the suture 100 to tissue. As mentioned above, in some embodiments, the barbs 118 can pass through the wall 115 of the hollow portion 112 and into tissue when the barbed portion 108 is disposed coaxially within the hollow portion 112, such as if the hollow portion's weave is loose and/or the barbs 118 are sufficiently long. All of the barbs 118, including the barbs 118 disposed within the hollow portion 112 and any barbs 118 disposed outside the hollow portion 112, can assist in securing the suture 100 to tissue, thereby helping to fix the tissue in an approximated position. In embodiments in which the length L2 of the barbed portion 108 is greater than the length L4 of the hollow portion 112, some of the barbs 118 can be positioned within the hollow portion 112 throughout the hollow portion's length L4, while others of the barbs 118 are positioned outside the hollow portion 112. These barbs 118 outside the hollow portion 112 can dig directly into tissue, as mentioned above. Depending on a size of the loop, the barbs 118 may not be positioned within the hollow portion 112 throughout its entire length L4, e.g., if a small loop is formed. In embodiments in which the length L2 of the barbed portion 108 is equal to or less than the length L4 of the hollow portion 112, all of the barbs 118 can be positioned within the hollow portion 112, as in the embodiment of FIG. 2 in which the barbed portion's length L2 is less than the hollow portion's length L4.

In some embodiments, the barbs 118 can be attached to the suture 100 via hinges (not shown). The hinges can be disposed at roots R of each of the barbs 118 (see FIG. 1). The hinges can be configured to facilitate collapsing of the barbs 118 radially inward against the suture 100 when the suture 100 is moved and/or tensioned in the first direction D1, and the hinges can be configured for the barbs to extend radially outward when the suture 100 is moved and/or tensioned in the second direction D2. The hinges can be biased such that the barbs 118 are biased to extend radially outward. The hinges can allow for rotational movement of the barbs 118 through a variable angular range with respect to the suture 100, for example from zero degrees up through the angle α. Additionally or alternatively, the suture 100 can have notches formed therein at the roots R, which can help to accommodate the barbs 118 when the barbs 118 are moved radially inward, e.g., when the suture 100 is moved and/or tensioned in the first direction D1. The notches can be sized such that the barbs 118 can be flush or substantially flush with the core portion of the barbed portion 108 when the barbs 118 are collapsed. The barbs 118 can be manufactured by stamping, and the notches can be formed in the barbs 118 during this stamping.

The barbs 118 can be made from one or more materials. The materials can be sufficiently rigid to allow the barbs 118 to securely grasp the wall 115 and/or tissue. Examples of the materials include plastics, e.g., polypropylene, prolene, etc, and/or metals, e.g., titanium, stainless steel, etc. The barbs 118 can have a filament threaded therearound to strengthen the barbs 118. The filament can be made from any one or more materials, but must be sufficiently thin to allow for passage of the barbed portion 108 through the passageway 116 and/or the wall 115 of the hollow portion 112. One exemplary suture that can be used as the barbed portion 108 is the Ethicon Stratafix™ barbed suture, available from Ethicon, Inc. of Somerville, N.J. The Stratafix™ barbed suture includes a barbed polymer or metal structure with a suture material, e.g., polyester, braided over the barbed polymer. The suture material can be braided over a partial or entire length of the polymer.

The suture 100 can be configured for use with a number of surgical devices and in a number of surgical procedures. By way of non-limiting example, a threader 120 can be used to splice the hollow portion 112 and to thread the barbed and/or leading portions 108, 106 therethrough. As shown in FIG. 1, an embodiment of the threader 120 can include a suture-engaging feature 122, a stem 124, and a pull tab 126. An entirety of the threader 120 can be configured to pass through the hollow portion 112. The threader 120 can be made from one or more materials that are sufficiently flexible to allow for passage of the threader 120 in through the wall 115 of the hollow portion 112, through at least a portion of the passageway 116, and out through the wall 115. In an exemplary embodiment, prior to use in a surgical procedure, the threader 120 can be inserted through the hollow portion 112 such that the stem 124 is positioned at least partially within the hollow portion 112, as shown in FIG. 2. Although the threader 120 can have any orientation when the threader 120 is at least partially within the hollow portion 112, in an exemplary embodiment the suture-engaging feature 122 of the threader 120 can extend through the wall 115 of the hollow portion 112 at a position adjacent to the trailing end 104, and the pull tab 126 can extend from an opposite end of the stem 124 and through the wall 115 at a position adjacent to the barbed portion 108. The suture-engaging feature 122 can be any feature configured to securely engage the leading end 102 of the suture 100. In the illustrated embodiment, the suture-engaging feature 122 is an eyelet having a size that allows for the passage of the suture 100, including the barbed portion 108, therethrough. The pull tab 126 can be configured to allow for gripping by a user to help pull a portion of the suture 100 that is mated to the suture-engaging feature 122 through the passageway 116 and/or the wall 115 of the hollow portion 112.

The suture 100 can be configured to approximate a variety of types of tissue, either the same or different from one another. Where the suture 100 is being used to approximate tissue that includes at least one bony structure, the suture 100 can be configured for use with a bone anchor. The bone anchor can be any bone anchor known in the art, and can be configured to secure the suture 100 to the bony structure. In particular, the bone anchor can have a suture-engaging feature, e.g., an eyelet, that is large enough for passage of the barbed portion 108 therethrough.

The suture 100 can be configured for use with an elongate tubular member to facilitate passage of the suture 100 through an incision in a patient's body and to a surgical site, such as in an arthroscopic procedure. The elongate tubular member can be, e.g., a trocar, delivery tube, endoscopic tunnel, cannula, etc, and can have a passageway therethrough extending between proximal end distal ends thereof. The passageway can be wide enough to allow at least two strands of the suture 100 to pass therethrough and can be long enough to extend between the incision and the surgical site.

The sutures disclosed herein can be generally used to approximate tissue without tying a knot in a variety of surgical procedures. For example, a suture can be used in a cuff repair procedure in which the suture is used to approximate tissues of a torn rotator cuff. In an exemplary embodiment, a barbed suture can be used to approximate two pieces of soft tissue.

In use, a suture can be inserted into a body of a patient in accord with customary surgical procedures, which can include open surgery or minimally invasive surgery, e.g., using a cannula. The suture 100 can be used, for example, in an exemplar) surgical procedure shown in FIGS. 3A-3D. Although this procedure is illustrated using the suture 100 and the threader 120 of FIG. 1, other sutures disclosed herein can be used and another threader or no threader can be used.

Figure 3A:
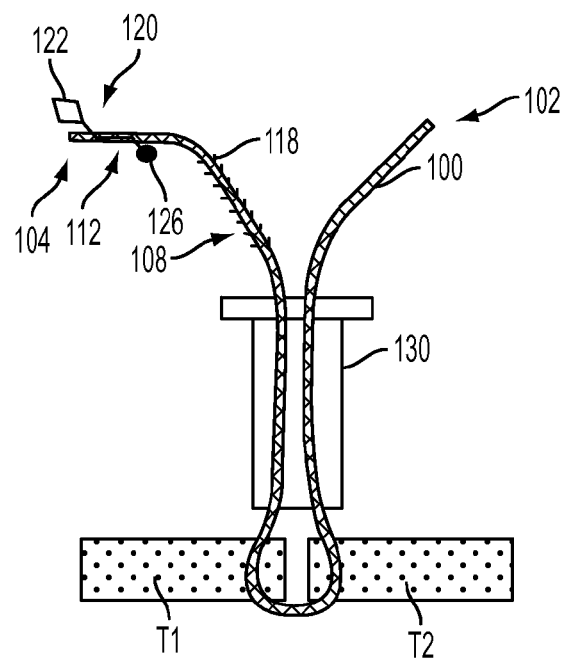
FIG. 3A is side schematic, partial cross-sectional view of the suture and the threader of FIG. 1 extending through a cannula, a first tissue, and a second tissue.

As shown in FIG. 3A, the leading end 102 of the suture 100 can be passed through a cannula 130, through a first soft tissue T1, through a second soft tissue T2, and back through the cannula 130 so as to have two strands of the leading portion 106 extending through the cannula 130. The suture 100 can be passed through the cannula 130 in any way, for example using a needle (not shown) attached to the leading end 102 of the suture 100. Although the cannula 130 is used to introduce the suture 100 into the patient's body in the illustrated embodiment, another cannula or other introducer device can be used to introduce the suture 100 into the body.

Figure 3B:
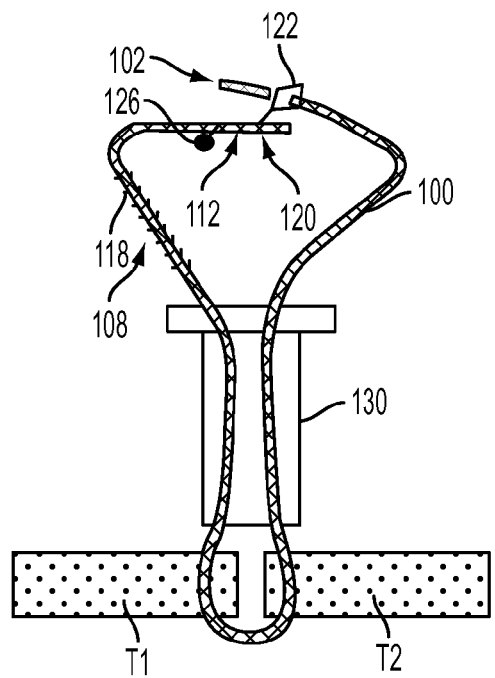
FIG. 3B is a side schematic, partial cross-sectional view of the suture, the threader, and cannula of FIG. 3A with a free end of the suture passed through the threader.
Figure 3C:
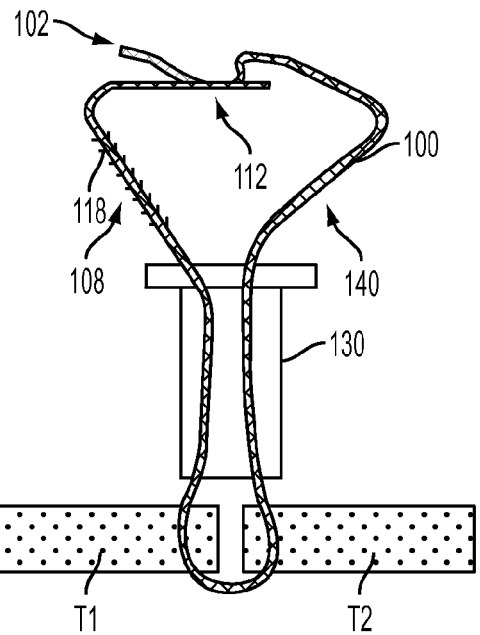
FIG. 3C is a side schematic, partial cross-sectional view of the suture and the cannula of FIG. 3B showing the threader removed and a portion of the suture extending through another portion of the suture to form a loop.
Figure 3D:
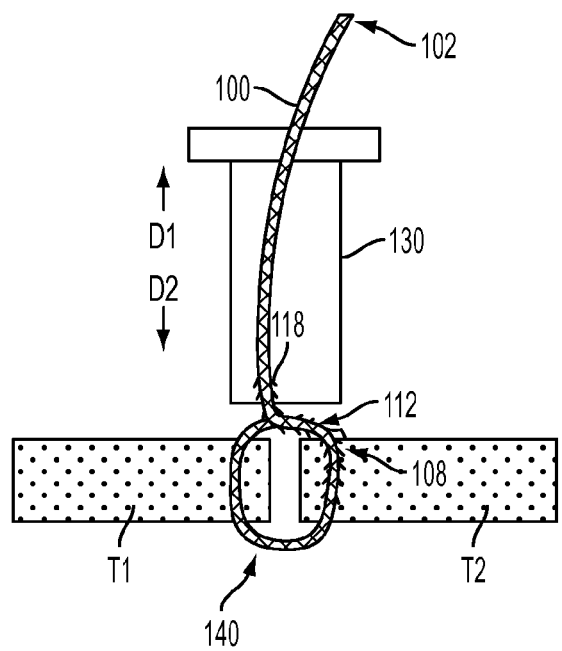
FIG. 3D is a side view of the suture and cannula of FIG. 3C showing the loop tensioned to secure the first and second tissues to one another.

The leading end 102 of the suture 100 can be mated to the suture-engaging feature 122 of the threader 120, e.g. by threading, as shown in FIG. 3B. The pull tab 126 of the threader 120 can be pulled, e.g., by a surgeon, a robotic controller, etc., to splice the hollow portion 112 and form a loop 140, as shown in FIG. 3C. The leading end 102 of the suture 100 can be pulled to adjust a size of the loop 140 to a desired size, for example to a size at which a user pulling the suture 100 feels sufficient tension in the suture 100. Because the barbs 118 all extend in the direction D1 in which the suture 100 is being pulled, the barbed portion 108 can pass easily through the wall 115 and the passageway 116 of the hollow portion 112. When the loop 140 has been reduced to the desired size, at least a part of the barbed portion 108 can be disposed within the hollow portion 112, as shown in FIG. 3D. As mentioned above, the barbed portion 108 can be coaxial with the hollow portion 112 when disposed therein, as shown in FIG. 3D. In the exemplary embodiment shown in FIG. 3D, the barbed portion 108 extends all the way through the length L4 of the hollow portion 112 so as to maximize the number of barbs 118 contained within the hollow portion 112. Thus positioned, the barbs 118 can grasp the wall 115 of the hollow portion 112 and/or the tissue T2 to prevent loosening of the loop. Additionally, the barbs 118 that are not positioned within the hollow portion 112 can help to secure the suture 100 in position by digging into the second soft tissue T2.

The barbs' resistance to movement can change depending on a direction of movement of the suture 100 and/or a tension that is applied to the suture 100. For example, as the barbed portion 108 passes through the passageway 116 of the hollow portion 112 in the first direction D1, the angle α of the barbs 118 with respect to the suture 100 can decrease, thus facilitating movement of the suture 100 in the first direction D1. Movement of and/or tension applied to the barbed portion 108 in the second direction D2 can cause the angle α of the barbs 118 with respect to the suture 100 to increase, thereby causing the barbs 118 to dig farther into the inner wall 115 and/or into tissue and increasing a resistance of the barbs 118 to movement in the second direction D2. Where tension is applied to the suture 100 in both the first and second directions D1 and D2, a diameter of the passageway 116 of the hollow portion 112 can decrease and/or the angle α of the barbs 118 with respect to the suture 100 can increase, both of which can cause the barbs 118 to dig deeper into the wall 115. In this way, the barbs 118 can provide strong resistance against any force and/or movement that would tend to cause the loop of the suture 100 to expand after the loop 140 has been tensioned to the desired size. The loop's desired size can vary for different tissues and/or different surgical procedures. In a cuff convergence procedure, the loop 140 can have a diameter in a range of about 10 to 15 mm.

Once the loop 140 of suture 100 has been reduced to the desired size, thereby securely approximating the tissue T1 and T2, the cannula 130 can be removed from the patient's body. In some embodiments, however, the cannula 130 can be removed before tightening of the suture 100 to form the reduced size loop 140. At least a portion of the leading portion 106 and/or the barbed portion 108 can be trimmed to remove excess suture from the surgical site.

A person skilled in the art will appreciate that the present invention has application in conventional minimally-invasive and open surgical instrumentation as well application in robotic-assisted surgery.

The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

One skilled in the art will appreciate further features and advantages of the invention based on the above-described embodiments. Accordingly, the invention is not to be limited by what has been particularly shown and described, except as indicated by the appended claims.

What is claimed is:

1. A surgical method, comprising:
 advancing a leading end of a suture through a cannula from a proximal end of the cannula that is located outside of a body to a distal end of the cannula disposed inside the body, proximate to a surgical site;
 advancing the leading end of the suture into a first tissue disposed inside the body;

advancing the leading end of the suture into a second tissue disposed inside the body;

advancing the leading end of the suture through the cannula from the distal end to the proximal end after advancing the leading end through the first and second tissue; advancing the leading end of the suture into and subsequently out of a hollow portion of the suture that is disposed outside of the body so as to form a loop such that a portion of the suture is coaxially disposed in the hollow portion, the portion of the suture disposed in the hollow portion being slidably movable relative to the hollow portion such that the portion of the suture disposed in the hollow portion is changeable; and pulling the leading end of the suture relative to the first tissue and the second tissue so as to advance the hollow portion through the cannula from the proximal end to the distal end so that the hollow portion is disposed inside the body, and to advance a plurality of unidirectional barbs formed on the suture through the first tissue, through the second tissue, and into the hollow portion, the plurality of unidirectional barbs grasping the suture within the hollow portion so as to lock the suture in position relative to the first and second tissues.

2. The method of claim 1, wherein pulling the leading end of the suture decreases a size of an opening defined by the loop.

3. The method of claim 1, wherein the unidirectional barbs are formed on the suture along a first partial longitudinal length of the suture that is longer than the hollow portion of the suture.

4. The method of claim 1, wherein a location of the suture with respect to the first and second tissues is locked without tying a knot in the suture and without using an additional attachment mechanism.

5. The method of claim 1, wherein advancing the leading end of the suture into a hollow portion of the suture, further comprises:

coupling the leading end to a suture-engaging feature of a threader, the threader being disposed in the hollow portion of the suture with the suture-engaging feature disposed on one side of the threader and an end configured to pull the threader on an opposed side of the threader, the suture-engaging feature being disposed more proximate to a trailing end of the suture than the end of the threader configured to pull the threader is disposed; and pulling the threader out of the hollow portion to advance the leading end of the suture into and subsequently out of the hollow portion such that the portion of the suture disposed in the hollow portion enters the hollow portion at a location that is more proximate to the trailing end of the suture than the portion of the suture disposed in the hollow portion exits the hollow portion.

6. The method of claim 1, wherein the length of the hollow portion and the barbed portion combined are less than the length of the remainder of the suture.

7. The method of claim 6, wherein the length of the hollow portion is in the range of about 5 mm to about 50 mm, the length of the barbed portion is in the range of about 10 mm to about 100 mm, and the length of the entire suture is in the range of about 100 mm to about 1500 mm.

8. A surgical method, comprising:

passing a leading end of a suture through a soft tissue, the suture having a plurality of unidirectional barbs formed on a portion thereof;

passing the leading end of the suture into a suture-engaging feature of a threader, the threader being disposed in a hollow portion of the suture with the suture-engaging feature disposed on one side of the threader and an end configured to pull the threader on an opposed side of the threader, the suture-engaging feature being disposed more proximate to a trailing end of the suture than the end of the threader configured to pull the threader is disposed;

pulling the end configured to pull the threader away from the hollow portion of the suture to pull the leading end of the suture into the hollow portion of the suture;

pulling the end configured to pull the threader away from the hollow portion of the suture to pull the leading end of the suture out of the hollow portion of the suture so as to form a loop around a portion of the soft tissue, the loop defining an opening thereof; and pulling the leading end of the suture to decrease a size of the opening and to position at least one of the plurality of unidirectional barbs in the hollow portion of the suture, wherein a size of the opening is maintained by the at least one of the plurality of unidirectional barbs positioned in the hollow portion engaging the suture.

9. The method of claim 8, wherein two or more unidirectional barbs of the plurality of unidirectional barbs are positioned in the hollow portion of the suture by pulling the leading end of the suture, and wherein the size of the opening is maintained by the two or more unidirectional barbs positioned in the hollow portion engaging the suture.

10. The method of claim 8, further comprising:

passing the leading end of the suture through a second tissue, wherein pulling the leading end of the suture to decrease a size of the opening defined by the loop draws the soft tissue and the second tissue towards each other.

11. The method of claim 10, wherein the leading end of the suture is passed into the hollow portion of the suture after the leading end of the suture has been passed through the soft tissue and passed through the second tissue.

12. The method of claim 8, wherein a length of the suture extending through the hollow portion is coaxial with the hollow portion.

13. The method of claim 8, further comprising:

advancing the leading end of the suture through a cannula from a proximal end of the cannula that is located outside of a body in which the soft tissue is located to a distal end of the cannula disposed inside the body, proximate to a surgical site, prior to passing the leading end through the soft tissue; and advancing the leading end of the suture through the cannula from the distal end to the proximal end after passing the leading end through the soft tissue.

14. The method of claim 13, wherein the steps of passing the leading end of the suture into a suture-engaging feature of the threader, pulling the end configured to pull the threader away from the hollow portion of the suture to pull the leading end of the suture into the hollow portion of the suture, and pulling the end configured to pull the threader away from the hollow portion of the suture to pull the leading end of the suture out of the hollow portion of the suture are performed outside of the body.

15. The method of claim 8, wherein the unidirectional barbs are formed on the suture along a first partial longitudinal length of the suture that is longer than the hollow portion of the suture.

16. The method of claim 8, wherein a location of the suture with respect to the soft tissue is locked without tying a knot in the suture and without using an additional attachment mechanism.

17. The method of claim 8, wherein the length of the hollow portion and the barbed portion combined are less than the length of the remainder of the suture.

18. The method of claim 17, wherein the length of the hollow portion is in the range of about 5 mm to about 50 mm, the length of the barbed portion is in the range of about 10 mm to about 100 mm, and the length of the entire suture is in the range of about 100 mm to about 1500 mm.

19. The method of claim 8, wherein the suture-engaging feature of the threader is disposed more proximate to the trailing end of the suture than the end of the threader configured to pull the threader is disposed, and thus, after the leading end of the suture is pulled out of the hollow portion of the suture, a portion of the suture disposed in the hollow portion enters the hollow portion at a location that is more proximate to the trailing end of the suture than the portion of the suture disposed in the hollow portion exits the hollow portion.

\* \* \* \* \*